United States Patent [19]

Sharma et al.

[11] Patent Number: 4,458,630
[45] Date of Patent: Jul. 10, 1984

[54] DISEASE CONTROL IN AVIAN SPECIES BY EMBRYONAL VACCINATION

[75] Inventors: Jagdev M. Sharma, Okemos, Mich.; Ben R. Burmester, Petaluma, Calif.

[73] Assignee: The United States of America as represented by the Secretary of Agriculture, Washington, D.C.

[21] Appl. No.: 391,065

[22] Filed: Jun. 22, 1982

[51] Int. Cl.³ .............................................. A01K 45/00
[52] U.S. Cl. ......................................................... 119/1
[58] Field of Search ............................................. 119/1

[56] References Cited

U.S. PATENT DOCUMENTS

| | | | |
|---|---|---|---|
| 2,477,752 | 8/1949 | Kiss | 119/1 |
| 2,851,006 | 9/1958 | Taylor et al. | 119/1 |
| 3,037,479 | 6/1962 | Flory | 119/1 |
| 3,120,834 | 2/1964 | Goldhaft et al. | 119/1 |
| 3,256,856 | 6/1966 | Nicely et al. | 119/1 |
| 3,377,989 | 4/1968 | Sandhage et al. | 119/1 |
| 4,040,388 | 8/1977 | Miller | 119/1 |

OTHER PUBLICATIONS

B. W. Calnek et al., "Modification of Marek's Diseases Pathogenicity by In Ovo Infection or Prior Vaccination," pp. 185–197, In: Viruses in Naturally Occurring Cancers, vol. 7, Cold Spring Harbor Conferences in Cell Proliferation, Cold Spring Harbor, New York (1980).
A. L. Romanoff, The Avian Embryo, Structural and Functional Development, The Macmillan Company, New York, pp. 1111 and 1121, (1960).
B. W. Calnek et al., "Field Trials With a Bivalent Vaccine (HVT and SB-1) Against Marek's Disease," Avian Diseases 27: 844–849, (1983).
J. M. Sharma et al., "Effect of In Vitro Adaptation of Marek's Disease Virus on Pock Induction on the Chorioallantoic Membrane of Embryonated Chicken Eggs," Infection & Immunity 13(1): 292–295, (Jan. 1976).
R. L. Witter, "Protection by Attenuated and Polyvalent Vaccines Against Highly Virulent Strains of Marek's Disease Virus," Avian Pathol. 11: 49–62, (1982).
Hitchner, "Virus Propagation in Embryonating Eggs," Chapter 37 in Isolation and Identification of Avian Pathogens, published by American Association of Avian Pathologists, pp. 120–121, (1980).
von Bulow, "Marek'sche Huhnerlahmung: Reaktionen im Experimentell Infizierten Embryonierten ei," Zbl. Vet. Med., B, 16: 97–114, (1969).

Primary Examiner—Hugh R. Chamblee
Attorney, Agent, or Firm—M. Howard Silverstein; David G. McConnell; Curtis P. Ribando

[57] ABSTRACT

Avian diseases, particularly those which threaten birds early in life, are controlled by embryonal vaccination during the final quarter of incubation. The site of inoculation may be either into the amnion, to include the amniotic fluid and the embryo itself, or else into the yolk sac. Protection afforded to chicks inoculated prehatch is four times or more than that of chicks inoculated post-hatch.

13 Claims, No Drawings

DISEASE CONTROL IN AVIAN SPECIES BY EMBRYONAL VACCINATION

BACKGROUND OF THE INVENTION

1. Field of the Invention

Marek's disease (MD) is a herpesvirus-induced lymphoproliferative disease that occurs naturally in chickens, and has been one of the leading causes of economic losses in the poultry industry. Since the advent of the turkey herpesvirus vaccine (HVT), newly hatched chicks have been routinely inoculated against the disease prior to being placed in the brooder houses. Although HVT vaccine is generally quite effective, occasionally inoculated flocks experience heavy MD losses. Several factors may be responsible for vaccine failure, including the possibility that chickens become exposed to virulent MD virus too soon after vaccination before they have developed adequate immunity. Similarly, neonate poultry chicks are susceptible to other common poultry pathogens despite first-day inoculation with vaccines. This invention relates to the control of disease in avian flocks by means of embryonic vaccination.

2. Description of the Prior Art

Taylor et al. (U.S. Pat. No. 2,851,006) teaches a method for increasing the hatch rate of bacterially infected eggs by means of in ovo treatment with a suitable bacteriophage. The phage is introduced to the interior of the egg prior to incubation by any of a variety of techniques including hypodermic syringe, pressure differential in a dipping fluid, and jet spray. By virtue of this technique, disease agents present in the extraembryonic membranes and fluids can be controlled by direct action of the inoculant. In U.S. Pat. No. 3,120,834, Goldhaft et al. expands the application taught in Taylor to a variety of substances including antibiotics, sulfonamides, vitamins, enzymes, nutrients, and inorganic salts. These agents in a liquid carrier are introduced through the shell prior to incubation by means of vacuum impregnation. Nicely et al. (U.S. Pat. No. 3,256,856) offers an improvement to the method of Goldhaft et al. in providing one or more holes in the egg shell for facilitating penetration. The hole is made in the air cell end of the egg, not extending beyond the inner shell membrane. The commercial practicality of the vacuum impregnation technique is limited by the unreliability of obtaining a uniform treatment and the economic unfeasibility of charging the dipping vats with expensive vaccines.

Miller teaches in U.S. Pat. No. 4,040,388 an automated method and apparatus for injecting embryonated eggs prior to incubation with a variety of substances. Injection is made into the albumen at the small end of the egg adjacent to the inner surface of the shell. The hole is thereafter sealed by coagulative cooking of the surrounding albumen. While the mechanics of the system are apparently functional, Miller fails to appreciate that the avian embryos prior to incubation have insufficient immunocompetence to benefit from the several vaccines contemplated for injection. Moreover, the vaccines are susceptible to inactivation during the heat coagulation step, and the albumen has an inhibitory effect on the transport of the inoculant to the embryo at the egg's opposite end.

SUMMARY OF THE INVENTION

We have now discovered that by proper selection of both the site and time of inoculation, embryonic vaccination can be effective in the control of poultry diseases. It is essential that the egg be injected during the final quarter of the incubation period, and that the inoculant be injected within either of the regions defined by the amnion or the yolk sac. Under these conditions, the embryo will favorably respond immunologically to the vaccine with no significant impairment of its prenatal development.

In accordance with this discovery, it is an object of the invention to control disease in avian flocks by initiating an immune response in the embryo, particularly in situations where post-hatch vaccination has proven not to be fully effective.

It is also an object of the invention to introduce a facile and efficacious technique for avian protection which obviates the injection of neonatal chicks.

Another object of the invention is to provide a method of embryonic vaccination amenable to automation and commercial application.

A further object of the invention is to inject avian eggs without adversely affecting the rate of hatchability of survival of hatched chicks.

Other objects and advantages of the invention will become readily apparent from the ensuing description.

DETAILED DESCRIPTION OF THE INVENTION

The method of this invention is applicable to any avian animal, whether domestic or wild, and particularly those which are commercially reared for meat or egg production. Without limitation thereto, exemplary avians include chickens, turkeys, geese, ducks, pheasants, and the like. Birds which are reared in high density brooder houses such as broiler and layer chickens are especially vulnerable to environmental exposure to infectious agents and would largely benefit from pre-hatch vaccination.

As discussed previously, one of the most prevalent and economically destructive diseases of the poultry industry is MD. The advantages of the invention are particularly apparent in the prevention of this and other lethal diseases which threaten avians early in life. In the broader sense, the scope of the inventive method is envisioned to extend to all immunizable avian diseases, whether of viral, bacterial, or other microbial origin. Examples of such, without limitation thereto, are avian leukosis, reticuloendotheliosis, infectious bronchitis, infectious bursal disease, Newcastle's disease, adenovirus diseases, reovirus, pox, laryngotracheitis, influenza, infectious coryza, fowl typhoid, and fowl cholera.

The term "vaccine" is defined herein in its broad sense to mean all types of biological agents used to produce active immunity. For most common avian diseases, the known vaccines designed for post-hatch administration would be used in accordance with the inventive method, adjusting the dosage as necessary.

Insofar as the mechanism for protection is dependent upon an immune response, the development of immunologic competence in the embryo is one of the critical determinative factors relating to the time of inoculation. As a general rule, this competence develops in the final quarter of the incubation period, before which the embryos are highly susceptible to infectious agents. We have found that by vaccinating prior to this stage, not only is the extent of protection in the neonate reduced, but also the vaccine may induce lesions in the embryo and/or extraembryonic membranes. For instance, prenatal chickens injected in earlier stages of development with HVT manifest an apparent immunosuppression and developed pathological lesions. While vaccination may be given anytime during the final 25% of the incubation period, it can be appreciated that the immunologic response is not immediate. For optimum protection of the hatchling, eggs should therefore be inoculated at least about 3 days prior to hatch. In the chicken, for example, this translates to injection by the eighteenth day of the 21-day incubation, corresponding to the time when embryonated eggs are routinely transferred to hatching trays. Injection could be conveniently combined with the transfer step.

Another critical consideration relating to the time frame for inoculation is the receptiveness of the inner egg structure to efficacious inoculation. As mentioned previously, the site of injection must either be within the region defined by the amnion, to include the amniotic fluid and the embryo itself, or else in the yolk sac. By the beginning of the fourth quarter of incubation, the amnion is sufficiently enlarged that penetration thereof is assured nearly all of the time when the injection is made from the center of the large end of the egg along the longitudinal axis. With a chicken egg in its eighteenth day of incubation, injection midway along, and perpendicular to, the longitudinal axis results in an amnion penetration frequency of about 80%, versus about 20% for the yolk sac. In the final quarter, the embryo is sufficiently developed and differentiated that it can tolerate the inherent randomization in the actual site of injection with no significant adverse effect on the rate of hatchability or on vital functions. Moreover, at this stage of incubation, the embryo is consistently positioned in the egg such that entry from the center of the large end will predictably result in injection in the upper dorsal region of the prenatal chick. Insofar as the embryo is bathed in the amniotic fluid and proceeds to ingest it during the final few days of incubation, vaccinal infection is readily initiated when the amniotic fluid receives the injection. Similarly, vaccine injected into the yolk sac infects the embryo during the yolk absorption process prior to hatch. Generally, the amniotic region is the preferred site of injection for the reason that the yolk may carry maternal antibodies which would have the effect of partially neutralizing non-cell associated vaccines.

The mechanism of injection is not particularly critical provided that it does not unduly damage the tissues and organs of the embryo or the extraemryonic membranes surrounding it. A hypodermic syringe fitted with a needle of about #22 gauge is suitable for the purpose. A 1-inch needle when fully inserted from the center of the large end will penetrate the shell, the outer and inner shell membranes enclosing the air cell, and the amnion. Depending on the precise stage of development and position of the embryo, a needle of this length will terminate either in the fluid above the chick or in the chick itself. A pilot hole may be punched or drilled through the shell in order to prevent damaging or dulling of the needle. In an automated system, it is envisioned that a penetrating device such as that taught by Miller, supra, would be effective. While it would not be desirable to apply heat to the needle as suggested therein to the extent of inactivating the vaccine or cooking any portion of the egg's interior, sterilization between injections would be beneficial in preventing cross-contamination. Alternatively, cross-contamination can be avoided by high pressure jet injection as known in the art of en masse human inoculation. It is usually unnecessary to reseal the hole after injection, though paraffin or the like would be suitable for the purpose.

Embryonal vaccination under the aforementioned conditions is characterized by a hatch rate comparable to untreated eggs. Any improvement in protection rate of prenatally inoculated chicks over post-hatch-inoculated chicks accordingly represents a positive improvement over the prior art. Resistance against MD of young birds from 18-day-vaccinated embryos challenged on the first 3 days post-hatch is up to about four times or more than that of birds vaccinated on the first day. The effect for later challenge is less dramatic in that the immune response in the 4-8-day-old chicks inoculated at hatch is roughly equivalent to that of the 1-day-old chick inoculated 3 days prehatch. Similar protection may be possible against other infectious diseases.

The following examples are intended only to further illustrate the invention and are not intended to limit the scope of the invention which is defined by the claims.

EXAMPLE 1

Embryonated White Leghorn chicken eggs were derived from a cross between line $15_5$ males and $7_1$ dams (15×7) from the flock maintained at the USDA Regional Poultry Research Laboratory in East Lansing, Mich. This flock was free of exposure to MDV, HVT, avian leukosis viruses, reticuloendotheliosis virus, and other common bacterial and viral poultry pathogens by appropriate serological tests. The eggs used for embryo vaccination, post-hatch vaccination, and as unvaccinated controls were all set at one time.

The vaccine used was a cell-associated preparation of strain FC126 of HVT (serotype III) propagated in chicken embryo fibroblast (CEF) tissue culture. The inoculum consisted of 0.1 ml. tissue culture medium containing 1000 plaque-forming units (PFU) of HVT. Test eggs were injected on the 18th day of incubation (3 days prior to hatch) by means of a 1-inch-long #22 gauge needle inserted through the side of the egg, approximately midway along the axis. The injection site was prepared by smearing with tincture of iodine or 80% methyl alcohol and drilling a small hole with a four-sided tapered punch. The entire length of the needle was inserted into the egg, and the inoculum was deposited. In hatched chicks, the vaccine was injected subcutaneously in the back of the neck.

The chickens were challenged by contact exposure accomplished by forcing the air from an isolator holding MDV-infected donor chickens into adjacent isolators containing recipient chickens. The donors consisted of 50 4-week-old 15×7 chickens, each inoculated at 1 day of age with 1700 PFU of MDV. The MDV was a cell-associated, tissue culture-propagated (ca/tcp) JM strain (serotype I). After 2 weeks of forced-air exposure, the recipient chickens were moved to clean cages.

Chickens that died during the experiment were necropsied. If no distinct gross lesions were found, sections of vagii, brachial and sciatic plexuses, gonads, and all suspect organs were fixed in 10% neutral "Formalin" and examined for histologic lesions. After 10 weeks, all surviving chickens were examined for gross lesions of MD.

The vaccine protection against MDV challenge was expressed as protective index, calculated as the percentage of MD is unvaccinated chickens minus the percentage of MD in vaccinated chickens divided by the percentage of MD in unvaccinated chickens and multiplied by 100. The results are reported in Table I, below.

EXAMPLE 2

The procedure of Example 1 was repeated except that the 18-day eggs were injected through the center of the large end, and the chickens were challenged by intra-abdominal injection of 1700 PFU MDV, JM strain. Also, in this experiment the chickens were sacrificed after 8–9 weeks for pathological examination. The results are reported in Table I, below.

EXAMPLE 3

The procedure of Example 2 was repeated except that the chickens were challenged with the ca/tcp Md-5 strain (serotype I) of MDV. The results are reported in Table I, below.

EXAMPLE 4

The procedure of Example 2 was repeated except that the chickens were challenged with the ca/tcp Ala-9 strain (serotype I) of MDV. The results are reported in Table I, below.

It is evident from the data in the Table for Examples 1–4 that chickens vaccinated as 18-day-old embryos were protected much better against early MDV challenge than were the chickens vaccinated at hatching. Chickens vaccinated at hatching and challenged 8 days later were fully resistant to the virus, indicating that lack of adequate protection against earlier challenge in chickens of groups vaccinated post-hatch was not due to defective vaccine or vaccination procedure.

EXAMPLE 5

The procedure of Example 2 was repeated except that the vaccine was the ca/tcp HN strain (serotype II) of MDV given at a dose of 410 PFU, and the dose of the JM challenge was 860 PFU. The results are reported in Table II, below.

EXAMPLE 6

The procedure of Example 5 was repeated except that the vaccine was the ca/tcp SB-1 strain (serotype II) of MDV given at a dose of 1015 PFU. The results are reported in Table II, below.

EXAMPLE 7

The procedure of Example 2 was repeated except that the vaccine was the ca/tcp MD-11-75C strain (serotype I) of MDV given at a dose of 1000 PFU and the challenge strain was the ca/tcp 287-L strain (serotype I) of MDV given at a dose of 1700 PFU. The results are reported in Table II, below.

EXAMPLE 8

The procedure of Example 2 was repeated except that the vaccine was a polyvalent vaccine given at a dose of 4000 PFU and comprising equal doses of MD-11-75C, SB-1, and HVT. The results are reported in Table II, below.

TABLE I

| Example | Time of HVT vaccination | Age (days) at MDV challenge | MDV challenge strain[a] | No. of chickens | % MD response (death & gross lesions) | Protective index |
|---|---|---|---|---|---|---|
| 1 | 18-day embryo | 0 | JM | 30 | 10 | 90[b] |
| | at hatch | 0 | | 27 | 78 | 22 |
| | at hatch | 8 | | 10 | 0 | 100 |
| | unvaccinated control | 0 | | 28 | 100 | — |
| | unvaccinated control | 8 | | 9 | 89 | — |
| 2 | 18-day embryo | 3 | JM | 14 | 7 | 93[b] |
| | at hatch | 3 | | 14 | 79 | 21 |
| | at hatch | 8 | | 11 | 0 | 100 |
| | unvaccinated control | 3 | | 13 | 100 | — |
| | unvaccinated control | 8 | | 3 | 100 | — |
| 3 | 18-day embryo | 3 | Md-5 | 14 | 29 | 71[b] |
| | at hatch | 3 | | 14 | 86 | 14 |
| | at hatch | 8 | | 5 | 20 | 78 |
| | unvaccinated control | 3 | | 13 | 100 | — |
| | unvaccinated control | 8 | | 12 | 92 | — |
| 4 | 18-day embryo | 3 | Ala-9 | 16 | 19 | 78[b] |
| | at hatch | 3 | | 14 | 71 | 17 |
| | at hatch | 8 | | 7 | 14 | 86 |
| | unvaccinated control | 3 | | 14 | 86 | — |
| | unvaccinated control | 8 | | 11 | 100 | — |

[a]In Example 1, challenge was by contact exposure; in Examples 2–4, challenge was by intra-abdominal injection.
[b]Protective index in embryo-vaccinated groups was significantly higher ($P < 0.001$) than that in groups vaccinated post-hatch and challenged at 3 days of age or at hatching.

TABLE II

| Example | Vaccine | Time of vaccination | Challenge strain | Age (days) at MDV challenge | No. of chickens | % MD response (death & gross lesions) | Protective index |
|---|---|---|---|---|---|---|---|
| 5 | HN | 18-day embryo | JM | 3 | 20 | 20 | 80[a] |
| | | at hatch | | 3 | 20 | 80 | 20 |
| | | at hatch | | 8 | 19 | 0 | 100 |
| | | unvaccinated control | | 3 | 20 | 100 | — |
| | | unvaccinated control | | 8 | 18 | 94 | — |
| 6 | SB-1 | 18-day embryo | JM | 3 | 20 | 20 | 80[a] |
| | | at hatch | | 3 | 20 | 95 | 5 |
| | | at hatch | | 8 | 14 | 0 | 100 |
| | | unvaccinated control | | 3 | 20 | 100 | — |
| | | unvaccinated control | | 8 | 20 | 80 | — |
| 7 | Md-11-75C | 18-day embryo | 287-L | 3 | 19 | 37 | 61[a] |

TABLE II-continued

| Example | Vaccine | Time of vaccination | Challenge strain | Age (days) at MDV challenge | No. of chickens | % MD response (death & gross lesions) | Protective index |
|---|---|---|---|---|---|---|---|
| | | at hatch | | 3 | 20 | 85 | 10 |
| | | at hatch | | 8 | 19 | 5 | 95 |
| | | unvaccinated control | | 3 | 20 | 95 | — |
| | | unvaccinated control | | 8 | 20 | 75 | — |
| 8 | polyvalent | 18-day embryo | 287-L | 3 | 19 | 0 | 100[a] |
| | | at hatch | | 3 | 19 | 89 | 11 |
| | | at hatch | | 8 | 19 | 0 | 100 |
| | | unvaccinated control | | 3 | 19 | 100 | — |
| | | unvaccinated control | | 8 | 19 | 72 | — |

[a]Protective index in embryo-vaccinated groups was significantly higher (P <0.001) than that in groups vaccinated post-hatch and challenged at 3 days of age or at hatching.

EXAMPLE 9

The procedure of Example 1 was repeated except that instead of challenging the chickens with MDV, they were sacrificed on the first day after hatch and analyzed for the presence of HVT viral antigen. From $1-2 \times 10^6$ spleen cells from individual chickens were inoculated in each of duplicate secondary monolayer cultures of CEF cells. The plaques were enumerated 3-4 days later. The results are reported in Table III, below.

EXAMPLE 10

The procedure of Example 9 was repeated except that white blood cells separated from heparinized blood were substituted for the spleen cells and the chickens were not sacrificed until the seventh day after hatch. The results are reported in Table III, below.

EXAMPLE 11

The procedure of Example 9 was repeated except that the 18-day eggs were injected through the center of the large end and the chickens were not sacrificed until the seventh day after hatch. The results are shown in Table III, below.

EXAMPLES 12A and 12B

To determine the effect of the age of the embryo at the time of inoculation on the hatchability of the eggs and the immune response to the chickens, embryos of the same crosses employed in the previous examples were injected at various days of the incubation period with 1000 PFU of the HVT vaccine. Chicks from embryos vaccinated at 11 days or older, as well as those vaccinated at hatch and the unvaccinated controls were challenged with the JM strain of MDV 3 days after hatch. The 8-day and 11-day eggs were vaccinated through the center of the large end, while the older eggs were injected through the side of the egg, approximately midway along the long axis. Hatched chicks were injected subcutaneously in the back of the neck. For each age group, the percentage eggs hatched was determined based upon 50-72 inoculated eggs.

Spleen cells were assayed for HVT antigen as described in Example 9. After 9 weeks post-hatch, the surviving chickens were sacrificed and examined for gross lesions. The results, reported below in Table IV, indicated that hatchability was adversely affected at the eighth and eleventh day of incubation. Moreover, it is evident that protection against MD is greatest when eggs are vaccinated with HVT at the seventeenth or the eighteenth day of embryonation. Decreased protection in chickens vaccinated at the nineteenth or the twentieth day of embryonation are presumably due to the short interval between vaccination and challenge.

EXAMPLE 13

In the course of a series of embryonal vaccinations with a variety of MDV strains in which 1264 eggs were vaccinated on the eighteenth day of incubation, 859 hatched, yielding a hatch rate of 68%. This compares favorably with the hatch rate of 69% (3060/4406) for uninjected eggs used as controls in the same series.

It is understood that the foregoing detailed description is given merely by way of illustration and that modification and variations may be made therein without departing from the spirit and scope of the invention.

TABLE III

| Example | Time of HVT vaccination | Age (days) when tested for virus | Source | HVT isolation +/tested | Titer (mean PFU/$10^7$ cells ±SEM[a]) |
|---|---|---|---|---|---|
| 9 | 18-day embryo | 1 | spleen | 5/5 | ND[b] |
| | at hatch | 1 | spleen | 0/5 | ND |
| 10 | 18-day embryo | 7 | white blood cells | 4/4 | 1520 ± 617 |
| | at hatch | 7 | white blood cells | 4/4 | 545 ± 83 |
| | unvaccinated control | 7 | white blood cells | 0/4 | 0 |
| 11 | 18-day embryo | 7 | spleen | 19/19 | 1278 ± 160 |
| | unvaccinated control | 7 | spleen | 0/10 | 0 |

[a]SEM = standard error of the mean.
[b]ND = not done.

TABLE IV

| Example | Time of HVT vaccination | % hatchability | +/tested | HVT isolation from spleen at 1 week Titer (mean PFU/$10^7$ cells ±SEM[a]) | No. of chickens | % MD response Death | % MD response Death & gross lesions | Protective index |
|---|---|---|---|---|---|---|---|---|
| 12A | 8-day embryo | 11 | 3/4 | 1409 ± 1065 | | | | |
| | 11-day embryo | 41 | 5/5 | 1495 ± 549 | 5 | 40 | 40 | 60[b] |
| | 14-day embryo | 62 | ND[c] | ND | 17 | 41 | 53 | 47 |
| | 16-day embryo | 74 | 4/5 | 1265 ± 396 | 19 | 10 | 31 | 69 |
| | 17-day embryo | 70 | 3/5 | 960 ± 561 | 22 | 4 | 14 | 86 |
| | 18-day embryo | 52 | 5/5 | 1708 ± 293 | 19 | 0 | 21 | 79 |
| | at hatch | 56 | 5/5 | 345 ± 97 | 19 | 47 | 68 | 32 |
| | unvaccinated control | 56 | 0/5 | 0 | 14 | 50 | 100 | — |
| 12B | 18-day embryo | 70 | ND | ND | 27 | 4 | 18 | 82 |
| | 19-day embryo | 61 | 2/2 | 551 ± 36 | 21 | 10 | 33 | 67 |
| | 20-day embryo | 63 | 3/3 | 1277 ± 707 | 23 | 22 | 43 | 57 |
| | at hatch | 72 | 2/2 | 1294 ± 159 | 20 | 50 | 85 | 15 |
| | unvaccinated control | 72 | 0/5 | 0 | 14 | 79 | 100 | — |

[a] SEM = standard error of the mean.
[b] This value is considered equivocal because of the small number of chickens at risk.
[c] ND = not done.

We claim:

1. A method for controlling an immunizable disease of viral, bacterial, or microbial origin in an avian species comprising injecting a vaccine effective for inducing immunity against said disease into the egg embodying the embryo of said avian species, wherein said injection is made during the final quarter of the incubation period whereby the embryo has developed immunologic competence and wherein said vaccine is injected within the region defined by either the amnion or the yolk sac.

2. A method as described in claim 1 wherein said vaccine is injected through the large end of the egg.

3. A method as described in claim 1 wherein said vaccine is injected into the amniotic fluid.

4. A method as described in claim 1 wherein said vaccine is injected directly into the embryo.

5. A method as described in claim 1 wherein said disease is a viral disease.

6. A method as described in claim 5 wherein said viral disease is oncogenic.

7. A method as described in claim 1 wherein said avian species is selected from the group of chickens, turkeys, ducks, geese, and pheasants.

8. A method as described in claim 7 wherein said avian species is a chicken and said injection is made on the seventeenth or eighteenth day of said incubation period.

9. A method as described in claim 8 wherein said disease is Marek's disease and said vaccine is HVT.

10. A method as described in claim 8 wherein said disease is Marek's disease and said vaccine is a polyvalent vaccine comprising HVT and the SB-1 strain of Marek's disease virus.

11. A method as described in claim 8 wherein said disease is Marek's disease and said vaccine is one or more cell-associated, tissue culture-propagated strains of Marek's disease virus.

12. A method as described in claim 11 wherein said vaccine is the SB-1 strain of Marek's disease virus.

13. A method for controlling an immunizable disease of viral, bacterial, or microbial origin in the rearing of an avian species comprising the steps:
   a. incubating an embryonated egg of said avian species under conditions suitable for embryonic development and for the hatching of said avian species from said egg at the termination of the incubation period;
   b. injecting into the egg a vaccine effective for inducing immunity in the avian species against said disease, wherein said injection is made during the final quarter of the incubation period whereby the embryo has developed immunologic competence and wherein said vaccine is injected within the region defined by either the amnion or the yolk sac; and
   c. allowing said avian species to hatch from said egg at the termination of said incubation period.

* * * * *